United States Patent [19]

Goodenough et al.

[11] 4,055,771
[45] Oct. 25, 1977

[54] TEST BODY FOR A SCANNING TOMOGRAPHIC ANALYTICAL APPARATUS

[75] Inventors: David John Goodenough, Myersville; Kenneth E. Weaver, Gaithersburg, both of Md.; Joseph G. Smrcka; William Clayman, both of Norwalk, Conn.

[73] Assignee: Alderson Research Laboratories, Inc., Stamford, Conn.

[21] Appl. No.: 735,801

[22] Filed: Oct. 26, 1976

[51] Int. Cl.² ............................................. G02B 5/00
[52] U.S. Cl. ................................. 250/505; 250/445 T
[58] Field of Search ................... 250/252, 445 T, 476, 250/505, 510

[56] References Cited

U.S. PATENT DOCUMENTS 3,509,337  4/1970  DeClerk et al. ............. 250/445 T X
3,657,534  4/1972  DeClerk et al. ............. 250/445 T X Primary Examiner—Davis L. Willis
Attorney, Agent, or Firm—Buckles and Bramblett

[57] ABSTRACT

A test body is provided for determining an operating characteristic of a tomographic apparatus of the type that scans a human body member with an X-ray beam along an edge of a slice through the member, accumulates data in electrical form which is representative of the variations in the intensity of X-ray transmission through the body during a plurality of scans and reconstructs a cross sectional image of the slice from the accumulated data. The body comprises an energy absorption means which is arranged in a predetermined configuration and is adapted for absorbing electromagnetic energy from an impinging X-ray beam. The body also includes support means for positioning the energy absorbing means between a scanning X-ray beam and a detector of the apparatus.

27 Claims, 16 Drawing Figures

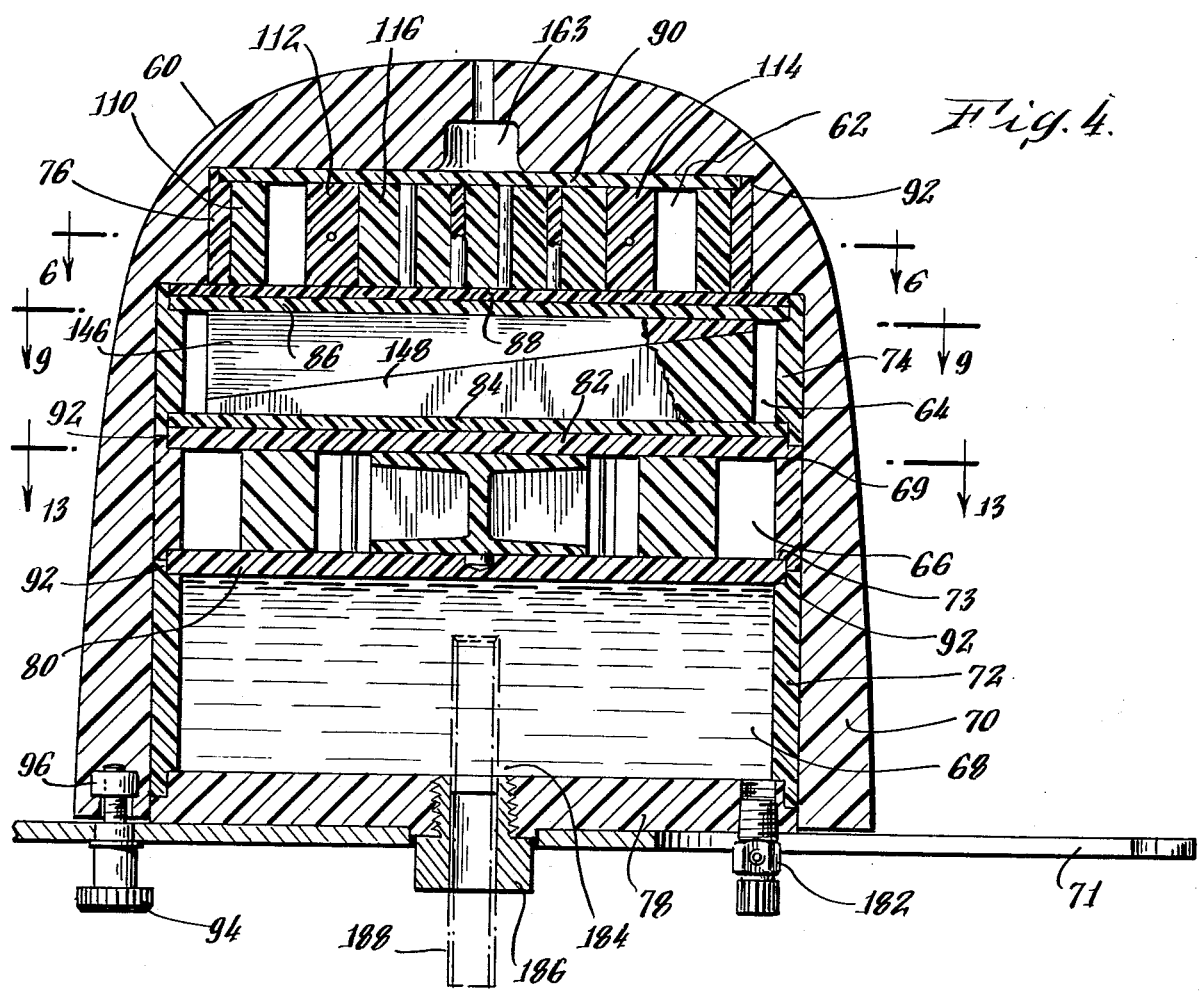
Fig. 4.
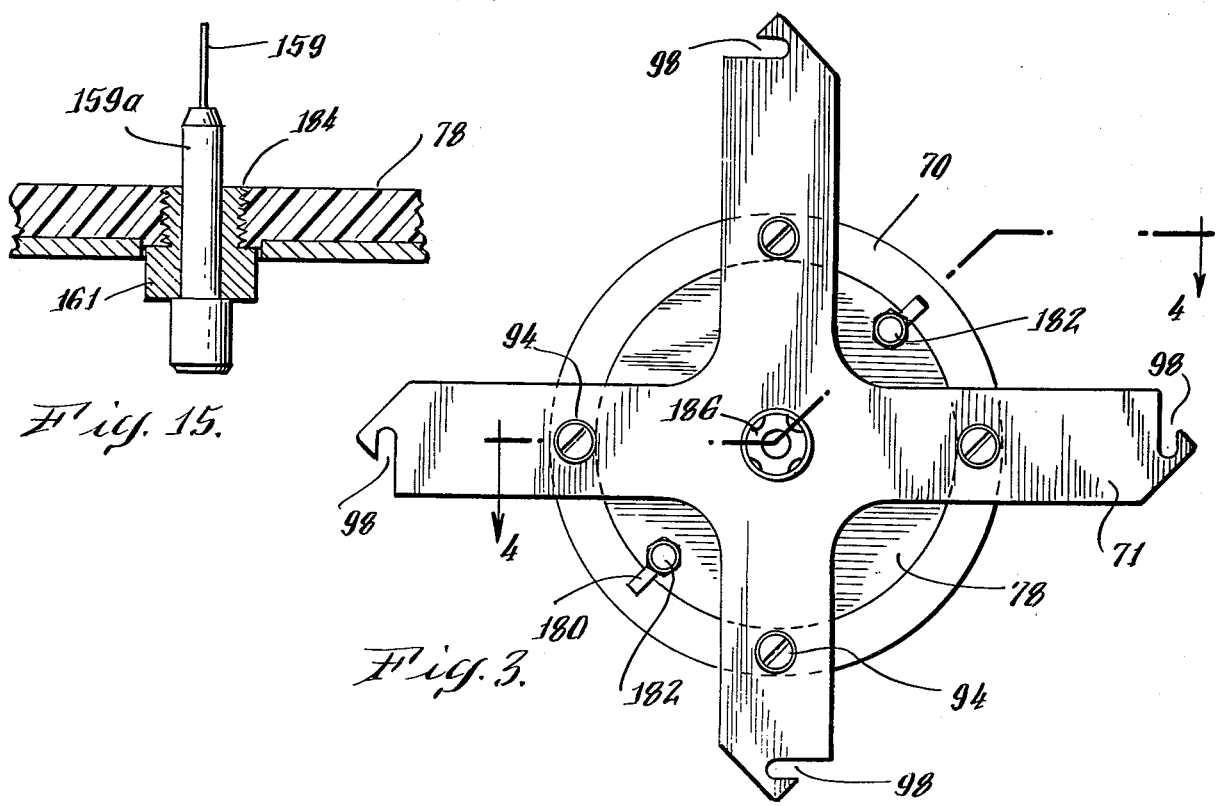
Fig. 15.
Fig. 3.

LINE PAIRS / CM

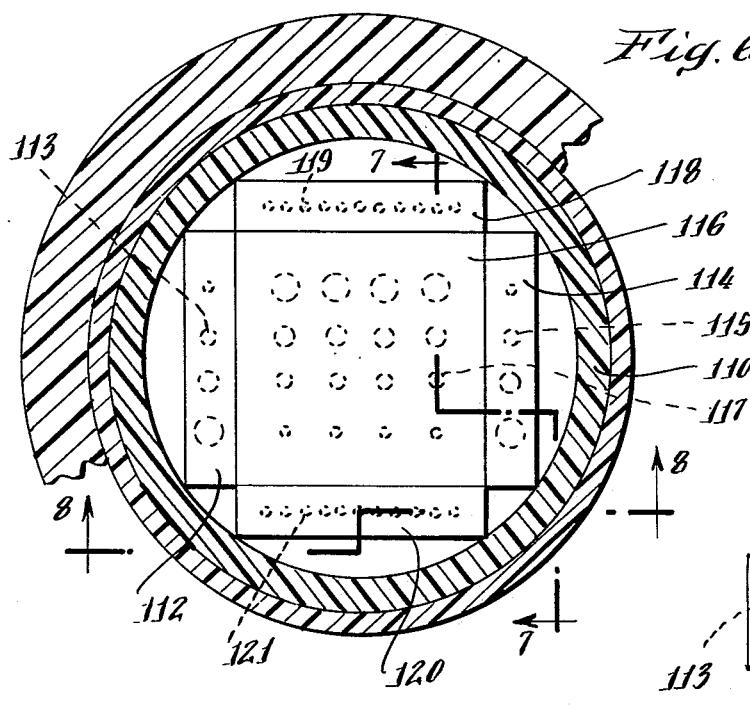
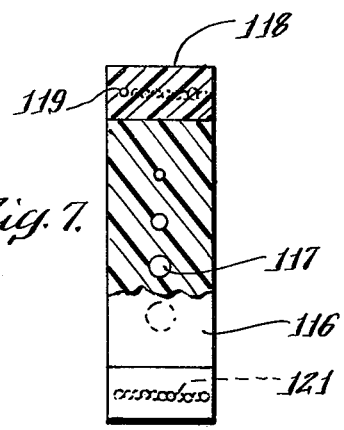
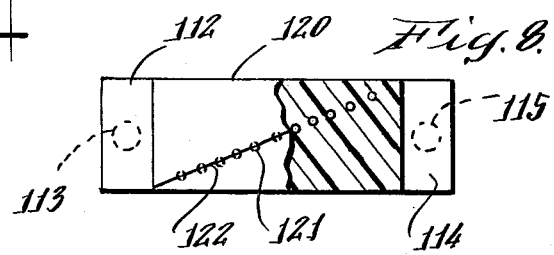
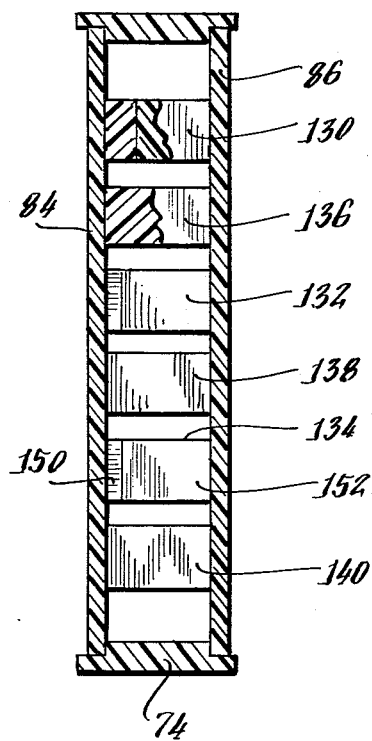
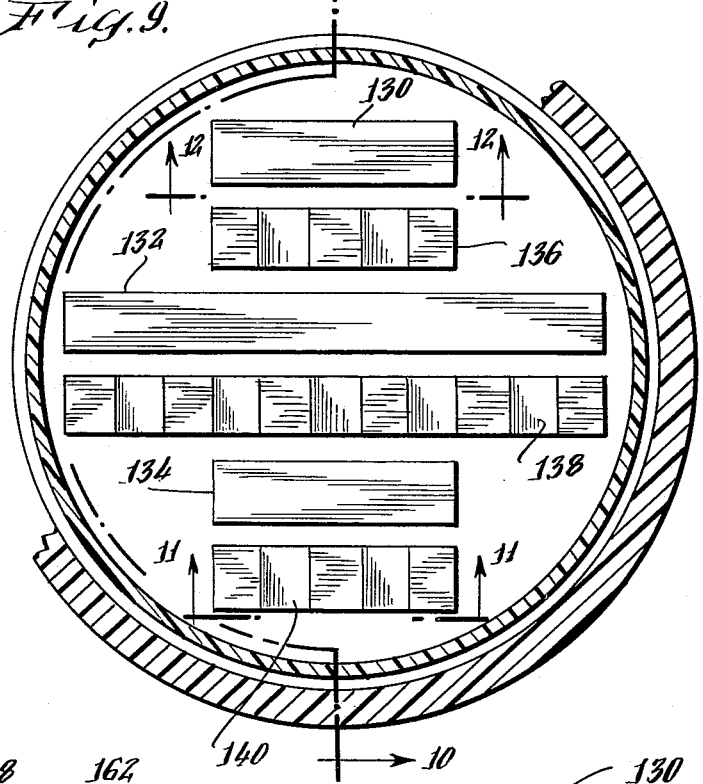
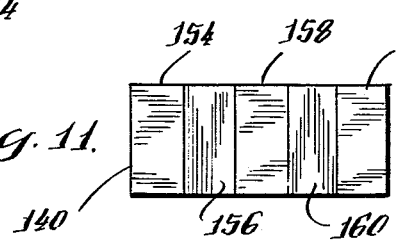
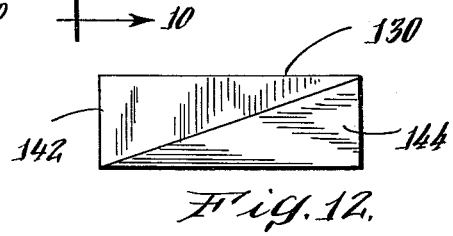

TEST BODY FOR A SCANNING TOMOGRAPHIC ANALYTICAL APPARATUS

BACKGROUND OF THE INVENTION

This invention relates to radiographic analysis. The invention relates more particularly to means for testing the operating characteristics of a tomographic analytical apparatus.

Tomography, as is well known, is a medical technique of radiographic analysis which provides an image of a particular plane of a body under examination. In one form of tomographic instrument, an X-ray source and an X-ray detector are positioned in alignment on opposite sides of a subject under examination and simultaneously scan an edge of a cross sectional plane or a slice of finite thickness extending through the subject. Intensity of X-ray transmission through the subject is determined by sampling an electrical output of the detector at a number of equally spaced positions in a single scan direction. Sampling occurs, for example, at about 160 different locations in the direction of a single scan. The X-ray source and detector are then rotated a predetermined angular distance about an axis normal to the plane or slice through the subject and another scanning of the edge in a different direction is obtained. In a form of this apparatus particularly adapted for examination of a patient's head, a scan occurs for each 1° of angular rotation. Resultant data is processed by a computer to reconstruct an image of the planar cross section or slice through the patient's head.

It is desirable at times to verify that the operation of a scanning tomographic instrument of the type described conforms with its known capabilities. In addition, it is desirable to predetermine the capabilities of the instrument for the performance of specific examinations.

Accordingly, it is an object of this invention to provide an improved means for testing the operation of a scanning, tomographic instrument.

Another object of the invention is to provide an improved phantom for verifying operating characteristics of a scanning tomographic instrument.

Another object of the invention is to provide a phantom simulating a human head and having means for verifying a plurality of operating characteristics of a scanning tomographic instrument.

SUMMARY OF THE INVENTION

In accordance with features of this invention, a test body is provided for determining an operating characteristic of a tomographic apparatus of the type which scans a human body member with an X-ray beam along an edge of a slice through the member, a cross sectional image of which is to be reconstructed, accumulates data in electrical form which is representative of variations in the intensity of X-ray transmission through the body during a plurality of scans and reconstructs a cross sectional image of the slice from the accumulated data. The body comprises energy absorption means arranged in a predetermined configuration and adapted for absorbing electromagnetic energy from an impinging X-ray beam and support means for positioning the energy absorbing means between a scanning X-ray beam and a detector of the apparatus. The test body, when scanned by the apparatus, provides predetermined energy absorption resulting in a predetermined absorption pattern. Upon reconstruction of a cross sectional image of the body by the apparatus, the reconstructed image and predetermined energy absorption patterns are compared to determine or to verify the operating characteristics of the apparatus.

In accordance with more particular features of the invention, the test body includes one or more cross sectional arrays each having one or more energy absorption test elements. The arrays are assembled in layers and each layer simulates a "slice" or cross sectional configuration of predetermined thickness. Scanning of a selected layer with an X-ray beam provides predetermined energy absorption which enables determination of particular characteristics of the apparatus. Such characteristics include, but are not limited to, detection by the apparatus of small objects at various contrast levels; detection by the appratus of small spherical "lesion-like" masses in a surrounding matrix; detection of small objects of varying sizes and contrasts; fidelity of a reconstructed image with respect to overlaps and voids between adjacent bands; resolution of the apparatus at various constrast levels; the generation of data for the determination of the modulation transfer function from the point spread function of the apparatus; the capability of the apparatus to distinguish between materials of different contrasts which do not have sharply defined edges; the capability of the apparatus to discriminate between materials of different absorptivities; the capability of the apparatus to determine the centering of rotation of the machines; the capability of the apparatus to produce spatially uniform scans; and the capability of determining the X-ray beam slice thickness.

THE DRAWINGS

These and other objects and features of the apparatus will become apparent with reference to the following specification and to the drawings wherein:

FIG. 3 is an end view of a support plate and test body constructed in accordance with features of this invention;

FIG. 4 is a sectional, elevational view taken along lines 4—4 of FIG. 3;

FIG. 6 is a section view taken along lines 6—6 of FIG. 4;

FIG. 7 is a view taken along lines 7—7 of FIG. 6;

FIG. 8 is a view taken along lines 8—8 of FIG. 6;

FIG. 9 is a view taken along lines 9—9 of FIG. 4;

FIG. 10 is a view taken along lines 10—10 of FIG. 9;

FIG. 11 is a view taken along lines 11—11 of FIG. 9;

FIG. 12 is a view taken along lines 12—12 of FIG. 9;

FIG. 15 is a fragmentary view of a section of FIG. 4; and,

DETAILED DESCRIPTION

Figure 1:
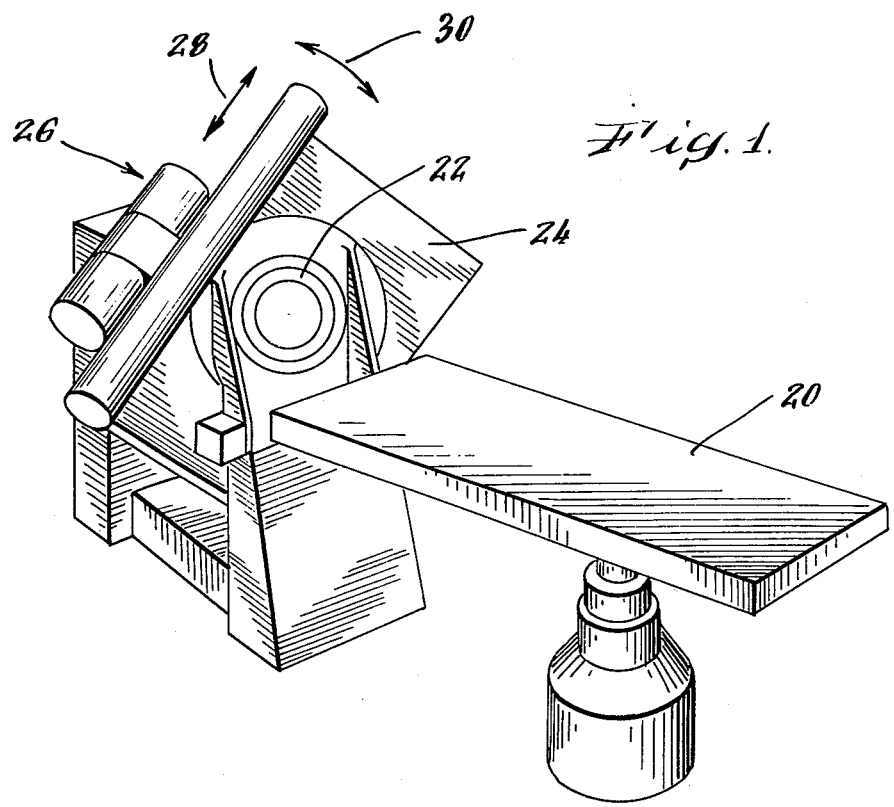
FIG. 1 is a perspective view of a scanning X-ray apparatus with which the test body of the present invention is utilized.
Figure 2:
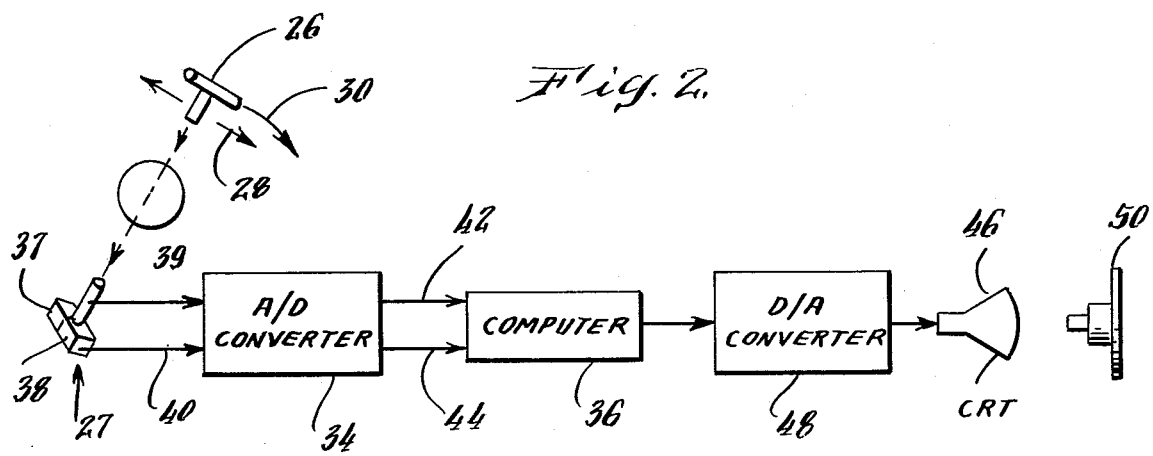
FIG. 2 is a schematic diagram illustrating the operation of the apparatus of FIG. 1.

FIGS. 1 and 2 illustrate a scanning tomographic apparatus with which the test body of the present invention is utilized. Although the apparatus of FIGS. 1 and 2 is principally utilized for the tomographic examination of parts of a subject's head such as the brain, the test body of the present invention is equally useful with and applicable to other forms of tomographic X-ray examination apparatus. In FIG. 1, a subject under examination is supported in a prone position on an examination table 20 and the subject's head is positioned within a generally circular shaped aperture 22 of the apparatus. The generally rectangular shaped member 24 of the apparatus is rotatable in angular increments about the subject's head. A source of X-rays is positioned in a generally cylindrically shaped member 26 and a detector means is positioned in the member 24 at an opposite position with respect to the cylinder 26 and the aperture 22.

Scanning the edge of a cross sectional plane or slice through the subject's head is performed by scanning linearly in the direction of the arrows 28 at a fixed rotary location of the member 24. During this linear scan, X-rays are projected in a beam at the side of the subject's head and a detector means is sampled at equally spaced intervals during the scan. The scanning assembly is then incremented in a rotary direction indicated by the arrows 30 and at each incremented location, a linear scan occurs. In particular, and during a linear scan, a collimated relatively narrow beam of X-rays is projected at the subject's head and toward the detector means 27 (FIG. 2) which is transported simultaneously with the source 26. The detector 27 comprises, for example, a sodium iodide crystal which scintillates or gives off photons of visible light when it is struck by X-rays photons from source 26. The amount of light emitted by the crystal is measured with a photomultiplier tube and is coupled through an analog-to-digital converter 34 to a memory unit of a digital computer 36. The relatively narrow X-ray beam provides for scanning a "slice" of the patient's head. Two adjacent slices may be scanned simultaneously and the detector 27 is shown to include two sensing devices 37 and 38 which are maintained in alignment with the X-ray source 26 during scanning. The detector means 27 provides electrical output signals from each of the sensing devices 37 and 38 which are coupled via lines 39 and 40 respectively to the analog-to-digital converter 34. These output signals are representative of the intensity of transmission of the X-ray beam through adjacent cross sectional planes or slices through the subject's head. The scanning digital data corresponding to the analog data of lines 39 and 40 is coupled via lines 42 and 44 respectively to the computer 36.

In a typical arrangement, the apparatus provides for 160 samplings during a linear scan and a semicircular scan at 1° increments through 180°. A linear scan is performed at each incremented rotary location to provide a total of 28,000 samplings for each scan slice. This data is stored by a storage unit of the computer 26 during sampling and upon completion of scanning, the data is processed by the computer to calculate about 6,400 different absorption values within each slice. These absorption values are provided in a cross sectional array representative of the absorption of the corresponding cross sectional slice of the subject's head. This cross sectional array is displayed as an image on a cathode ray tube 46 to which the image data is applied from the computer 36 through a digital-to-analog converter 48. The image can be copied by a camera 50 for permanent recording. Alternatively, the cross sectional array may be displayed as a printout of absorption values. This tomographic technique is well known and is described in further detail in *Scientific American,* October 1975, pages 56 through 68.

As indicated hereinbefore, it is desirable at times to determine and to verify the operating characteristics of a tomographic X-ray scanning apparatus. A test body 60 is provided in accordance with the present invention, which when scanned by a properly operating tomographic apparatus causes the apparatus to reconstruct a cross sectional image having a predetermined X-ray energy absorption pattern. This known pattern is compared with an actual pattern generated when the test body is scanned by a tomographic apparatus being tested for determining and verifying the operating characteristics of the latter apparatus. The test body comprises an energy absorption means of predetermined absorption characteristics and means for positioning the energy absorption means at a location between the X-ray source and the detector so that a projected X-ray beam impinges the test body. The absorption means comprises one or more energy absorption elements, described hereinafter, each having a predetermined energy absorption characteristic. The absorption elements are positioned in one or more arrays 62, 64, 66 and 68 (FIG. 4) each of which represents a slice or piece of finite thickness through the test body. The arrays are assembled in layers which are supported in position between the X-ray source 26 and the detector 27 (FIG. 2) by means comprising a housing 69 and a base plate 71. A shell 70 is also provided which imparts to the test body 60 the general shape of a human head and facilitates positioning of the test body in a tomographic apparatus of a type having a receptacle conforming with the shape of a human head. Upon scanning a "slice" through an array of energy absorption means, the tomographic scanning apparatus described hereinbefore will generate an image of predetermined configuration. The particular configuration is determined by the selected array through which the scanning is performed. As indicated hereinafter, the different arrays of test elements provide testing of different characteristics of the apparatus.

Figure 5:
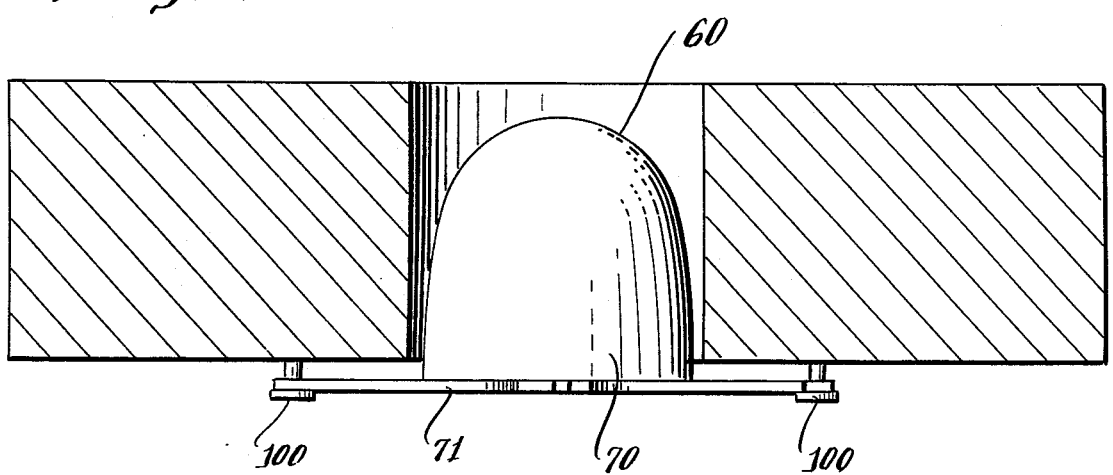
FIG. 5 is a view, partly in section, illustrating the mounting of the test body of FIG. 4 to the apparatus of FIG. 1.

Referring now to FIG. 4, the housing 69 comprises an assembly of a plurality of cylindrically shaped wall members 72, 73, 74 and 76, a water chamber base plate 78 and circular support members 80, 82, 84, 86, 88 and 90. The wall members have ridges 92 formed therein which, when arranged in a stacked assembly as shown, provide notches for receiving and captivating the cross sectional support members. There is positioned between the different cross sectional support members a plurality of energy absorption test elements, such as elements 112, 114 and 116 which are positioned between plates 88 and 90. The shell 70 is positioned about the housing assembly 69 and is secured to the plate 71 by a plurality of screws 94 which engage nuts 96 located at different angular positions about a lower portion of the shell 70. As indicated in FIGS. 3 and 5, the plate 71 includes notches 98 which engage screws 100 for supporting the test body 60 in the apparatus between the scanning X-ray beam source and detectors.

Referring now to FIGS. 4, 6, 7 and 8, the array 62 of test elemens is shown to include a test element comprising a cylindrically shaped ring 110, test elements comprising first and second rectangular shaped volume contrast sensitivity bars 112 and 114 respectively, a test element comprising a generally square shaped contrast detail body 116 and test elements comprising first and second rectangular shaped slice geometry bars 118 and 120 respectively. These bodies are formed of materials which absorb electromagnetic energy in the X-ray spectrum. Exemplary materials are polymer plastics which are formed by molding or casting. Particular materials and their desired characteristics are described in greater detail hereinafter. First and second pluralities of linearly extending spherically shaped bodies 113 and 115 are located within the first and second bars 112 and 114 respectively. The spherical bodies 113 and 115 extend linearly in a direction generally parallel to a horizontal plane of the layer 62 as viewed in FIG. 4. A plurality of spherically shaped bodies 117 is positioned in the body 116 and are arranged in a generally rectangular shaped matrix. The bar shaped bodies 118 and 120 each include pluralities of spherically shaped bodies 119 and 121 respectively which extend linearly and slope at an angle with respect to the horizontal plane of the layer 62. The spherically shaped bodies 113 and 115 of the volume contrast sensitivity bodies 112 and 114 respectively and the spherically shaped bodies 117 of the contrast detail body 116 are of progressively increasing diameter. The spherically shaped bodies 119 and 121 of the slice geometry bars 118 and 120 respectively are of the same general diameter and, as seen in FIG. 8, slope with respect to the horizontal plane of the layer 62. Positioning of the spherical bodies in associated test elements is accomplished by molding or casting the same within the test element body. Suitable materials from which the spherically shaped bodies are fabricated are described in detail hereinafter. On the external surface of each of bars 118, 120, there is cemented a tinned copper wire 122 of 0.010 inch diameter which parallels the bodies 119, 121. Support for the absorption test elements 110-120 is provided by positioning these test elements between the support members 88 and 90 by which they are maintained in position through frictional contact with these support members.

The test element array 64 illustrated in FIGS. 4, 9, 10, 11 and 12 includes a plurality of test elements comprising a plurality of rectangular, bar shaped sensitometric wedge bodies 130, 132, and 134, and a plurality of rectangular bar shaped contrast sensitivity bodies 136, 138 and 140. The bodies 130, 132 and 134 are formed by juxtaposed wedges which present a continously varying contrast to a scanning X-ray beam. Wedge segments 142 and 144 (FIG. 12) of body 130 provide an X-ray beam target of relatively high contrast. The wedge segments 146 and 148 (FIG. 4) of the bar 132 provide an X-ray beam target of medium contrast and the bar 134 includes wedge shaped segments 150 and 152 (FIG. 10) which presents a relatively low contrast target to the scanning X-ray beam. The contrast sensitivity bars 136, 138 and 140 are composite bars formed of bar segments, as illustrated in FIG. 11 by segments 154, 156, 158, 160 and 162. These bars test the capability of the apparatus to distinguish between materials of different absorptivities over different contrast ranges. The bars 130-140 provide predetermined characteristics which, when scanned by the X-ray beam, will generate an image having a predetermined configuration. These bars are secured in position between the cross sectional support members 84 and 88 of the housing assembly. Suitable materials from which these bars are fabricated are described hereinafter.

Figure 13:
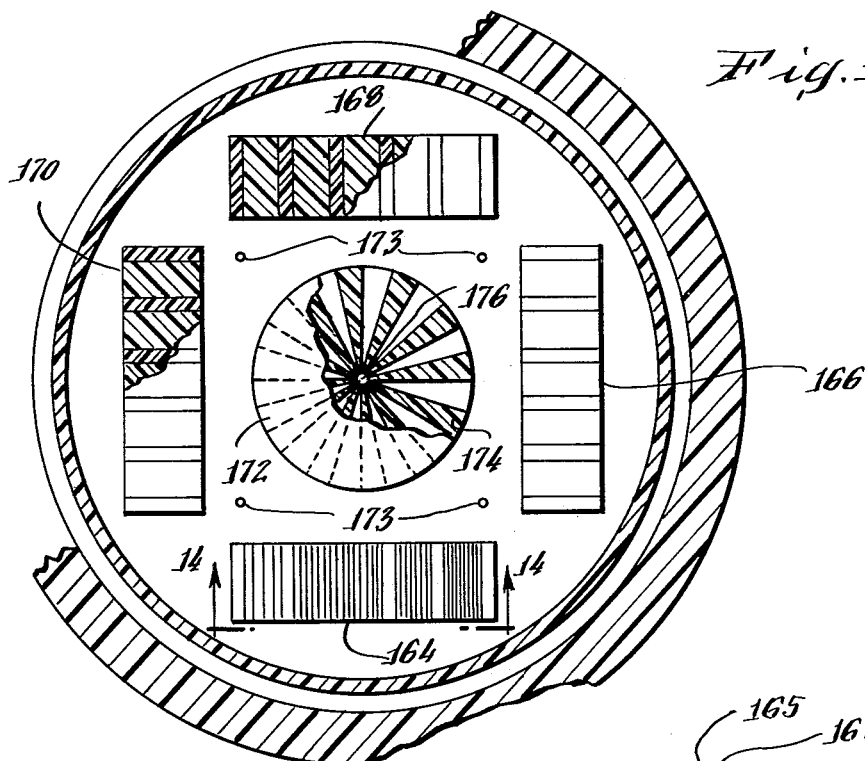
FIG. 13 is a fragmentary view, partly broken away, taken along lines 13—13 of FIG. 4.
Figure 14:
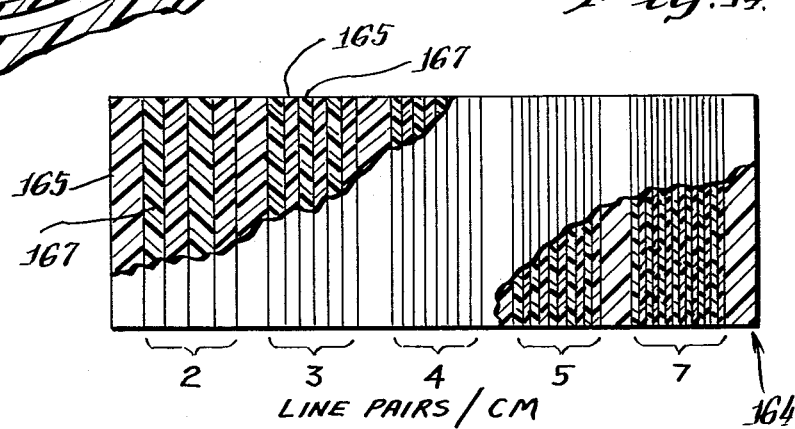

The test element array 66, illustrated in FIGS. 4, 13 and 14, includes test elements comprising generally rectangular bar shaped resolution bodies 164, 166, 168 and 170, a star shaped body 172, and a plurality of vertically positioned wires 173. Each of the resolution bodies 164-170 is formed of parallel sheets of material of selected thickness to produce fine line pairs. The sheets are formed of two types of material which are alternated in position, as illustrated in FIG. 14, by sheets 165 and 167, to provide a difference in contrast at the juncture of their surfaces. Thickness of these sheets is also varied to provide a variation in the number of pairs in a centimeter. The bodies 164, 166, 168 and 170 present low, medium, intermediate high, and high contrasts respectively to a scanning X-ray beam. The star shaped test element 172 comrpises a twelve point siemens star having a plurality of segments 174 extending radially from a hub 176. This body is provided for determining resolution at relatively high contrast levels. The four metal wires 173, which are vertically oriented, have a relatively small diameter on the order of 0.010 inch and are provided for determining the modulation transfer function of the apparatus at different locations in a "slice". The test element array comprising the resolution bars 164, 166, 168 and 170, along with the siemens star 172, and the wires 173 are secured between the support cross plates 80 and 82. These members are fabricated of suitable materials described hereinafter.

A fourth array includes a test element comprising a fluid bath formed by the cylindrically shaped housing wall member 72 (FIG. 4), the plate 78 and the support cross plate 80. The fluid contained in the bath is generally a liquid such as water. The members 72, 78 and 80 are arranged in a fluid tight configuration for inhibiting leakage of a fluid which is contained therein. The fluid contained in the bath is introduced and drained or can be continuously flowed through the bath via control valve inlet fittings 180 and 182 (FIG. 3). An access port 184 is provided and a wall thereof is internally threaded to receive a plug 186 or, alternatively, a specimen holder 188 shown dashed in FIG. 4 or a pin for determination of centering of rotation, or the point spread function of the apparatus. The specimen holder comprises a tubular body which is adapted to contain and position a specimen within the bath chamber during scanning. The specimen holder 188 is press fitted in a threaded nut and provides a fluid type seal between the specimen holder 188, the plug 186 and the members of the bath.

A pin 159 on a stem 159a (FIG. 15) is provided for indicating uniformity of rotation of the apparatus or point spread function of the apparatus. The pin 159 is mounted alternatively to the specimen holder 188 and the plug 186. Its stem 159a is press fitted into a threaded nut 161 and extends into the fluid bath chamber. The nut 161 is positioned in the access port 184.

The various test bodies described are selected to provide predetermined physical characteristics which test the operating characteristics of the tomographic scanning apparatus. While various materials and configurations may be selected to suit the various testing requirements of the apparatus, the following exemplary materials provide for the desired testing of the indicated characteristics of the layered absorption means. In the array 62, the cylindrically shaped body 110 is provided to stimulate the effect of the skull on data obtained as well as capability of the machine to distinguish relatively small objects at various contrast levels. A preferred material comprises (TEFLON) polytetrafluoroethylene. Other suitable materials comprise pigment filled plastics such as polyester, polystyrene, polyurethane, etc. which have been adjusted to provide a CT number of +500. As used herein, the term "CT" refers to numbers which are related to an X-ray linear attenuation coefficient averaged over the various energies in the photon spectrum. The scale employed ranges from −500 for air, 0 for water, to +500 for bone. The volume contrast sensitivity bars 112 and 114 and their associated spherical bodies 113 and 115 respectively are provided for testing the ability of the apparatus to distinguish relatively small spherical lesion-like masses in a surrounding matrix. The bar 112 comprises a polyester matrix in which the bodies 113 positioned therein are formed of TEFLON (polytetrafluoroethylene), are spherically shaped, and have outside diameters progressively increasing in size such as 1/16 inch, 3/32 inch, ⅛ inch and 3/16 inch. The volume contrast sensitivity bar 114 comprises a polyester matrix in which the bodies 115 positioned therein are formed of nylon, are spherically shaped, and have outside diameters of progressively increasing size such as 1/16 inch, 3/32 inch, ⅛ inch and 3/16 inch. The bar 112 is a relatively high contrast target since the TEFLON balls exhibit a CT number of about +480 while the polyester matrix exhibits a CT number of about +60. The bar 114 is a relatively low contrast target since the nylon balls exhibit a CT number of about +44.7 while the polyester matrix exhibits a CT number of about +60.

The contrast detail target 116 tests the capability of the apparatus to distinguish relatively small objects of varying sizes and contrasts. The target body 116 is formed of a castable surround polymer such as polyurethane having a CT number of about +14 while the spherical bodies 121 are formed of materials selected from the group including TEFLON, nylon, polypropylene and air having CT numbers of +480, +48, −60 and −500 respectively.

The bar shaped slice geometry test elements 118 and 120 are adapted to test the fidelity of the reconstructed image within a slice. In this regard, voids or information missing from the reconstructed image is detected. In addition, these elements are adapted to test for overlaps of the scanning X-ray beam between adjacent slices, which may occur in the reconstructed image. These test elements are formed of any castable plastic and the pluralities of internally contained bodies 119 and 121 are generally spherically shaped and are of a same diameter. They extend linearly at an angle with respect to the plane of the layer 62. These bodies are formed of a relatively high contrast material. Suitable materials are steel and sapphire. The wire or bar 122 slopes similarly.

A target which varies continuously in CT number is presented to the scanning X-ray beam by the sensometric wedge test elements 130, 132 and 134. These test elements are utilized to determine the capability of the machine to distinguish materials of different contrasts but wherein the boundary between the materials does not exhibit sharply defined edges. The wedge segments 142 and 144 of wedge body 130 provide relatively high contrast. The wedge segment 142 is formed, for example, of polyurethane foam, polystyrene foam or urea foam, each of which has a CT number of about −300. The wedge segment 144 is formed, for example, of TEFLON, halar or kelf having a CT number of about +480, +460 and +700 respectively to provide a difference in CT number with respect to the wedge segment 142 of about 780, 760 and 1,000 respectively. The wedge test element 132 comprises a medium contrast wedge and the wedge segments 146 and 148 thereof are formed, for example, of LEXAN and LTPE respectively having CT numbers of about +52 and −51 respectively to provide a contrast differential of 100. The wedge test element 134 provides relatively low contrast to the scanning X-ray beam and its wedge segments 150 and 152 thereof are formed of LEXAN and PMMA or polyester having CT numbers of about +52, +63 and +60 respectively to provide a differential in contrast of approximately 11 or 10.

Contrast sensitivity step bars 136, 138 and 140 (FIG. 9) determine the capability of the apparatus to distinguish objects of known CT numbers and to determine its degree of accuracy. These bars also test the capability of the machine to discriminate between materials of different absorptivities. The bar 140 provides relatively low contrast and the segments 154, 156, 158, 160 and 162 are selected to have CT numbers of about −10, −5, 0, +5 and +10 respectively. The bar 138 provides relatively medium contrast and its segments have CT numbers extending in value from about −50 to +50 and incrementing by a difference of 10. The bar 136 provides relatively high contrast and its segments have CT numbers of about −400, −200, 0, +200 and +400. Materials from which the bars can be fabricated and their CT numbers are:

| CT Number | Material | CT Number | Material |
|---|---|---|---|
| −50 | L. D. Polyethylene (LDPE) | +10 | HDPE plug Tefzel (ETFE) |
| −40 | LDPE Polyethylene plus HD polyethylene (HDPE) | +20 | " |
| −30 | HDPE plus Tefzel (ETFE) | +30 | " |
| −20 | " | +40 | " |
| −10 | " | +50 | " |
| −5 | " | +200 | " |
| +0 | " | +400 | Tefzel plus Halar (ECTFE) |
| +5 | " | | |

The resolution bars 164, 166, 168 and 170 determine the resolution capability of the apparatus at various contrast levels. The low contrast bar 164 is formed by parallel plastic sheets of material comprising LEXAN having an average CT number of about 52 and nylon having an average CT number of about 45 to provide a differential of 7. The medium contrast bar 166 was formed of nylon and polystyrene, the latter having a CT number of about −14 to provide a differential of 59. The intermediate high contrast bar 168 was formed of LEXAN and polyethylene, the latter having a CT number of about −51 to provide a differential of 103. The high contrast bar 170 was formed of filled polystyrene having a CT number of about +480 and polystyrene having a CT number of about −14 to provide a differential of about 494. The Siemens star 172 is formed of a castable material with a CT number in the range of about +400 to +500. One suitable castable plastic material is a filled polyester.

The housing shell 70 is formed of any castable plastic, one such suitable material being urethane. The shell 70 provides a head contour suitable for X-ray scanning apparatus of the water bath type.

Figure 16:
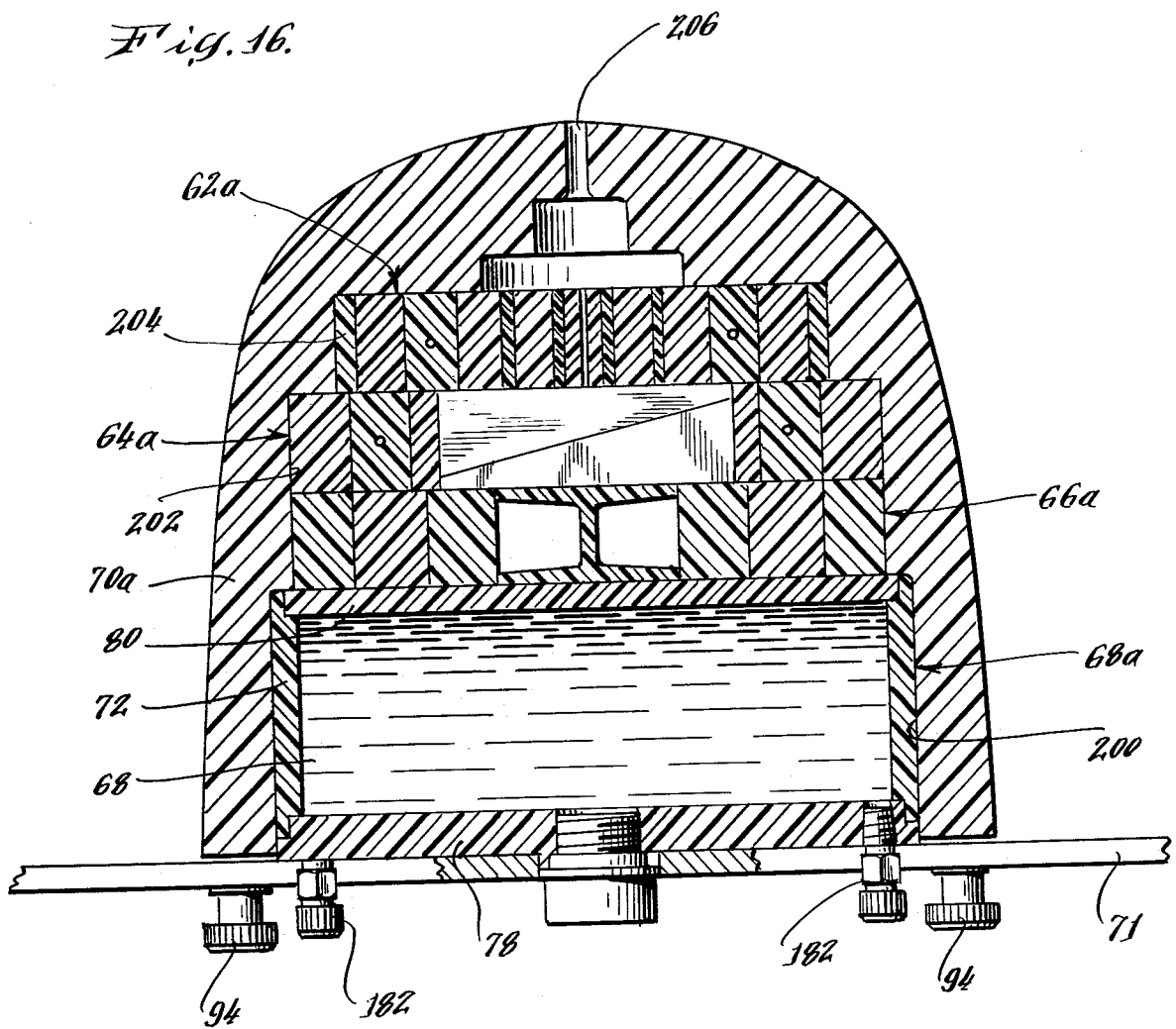
FIG. 16 is a cross sectional elevational view of a modified version of the apparatus of the invention.

In FIG. 16 there is illustrated a modified form of construction which eliminates the need for many of the purely structural elements. In this modification, the shell 70a is molded with a plurality of recesses 200, 202, 204 and an air vent 206. Each array 62a, 64a, 66a is potted in a disc of suitable plastic and the discs are inserted into the recesses, air escaping through vent 68a. The array 206 comprises a cylindrical water chamber. The mounting bolts 94 engage nuts captured in the material of shell 70a.

A test body has thus been described which advantageously provides predetermined absorption characteristics for testing the operational characteristics of an X-ray scanning tomographic apparatus. The test body comprises an energy absorption means and means for positioning the body in the path of the scanning X-ray beam of a tomographic apparatus. The test body is advantageous in that it provides in situ testing of the the apparatus to assure the operating capability of the apparatus.

While there has been described various embodiments of the invention, it will be apparent to those skilled in the art that variations may be made thereto without departing from the spirit of the invention and scope of the appended claims.

We claim:

1. A test body for determining an operating characteristic of a tomographic apparatus of a type which is adapted to scan a human body member with an X-ray beam along an edge of a slice through the member, accumulate data in electrical form during the scanning which is representitive of variations in the intensity of the transmission of X-ray energy through the member during a plurality of scans, and reconstruct a cross sectional image of the slice from the accumulated data comprising:
   A. energy absorption means arranged in layered arrays, each array extending generally parallel to a direction of projection of the X-ray beam and comprising one or more energy absorption test elements adapted for absorbing electromagnetic energy from an impinging X-ray beam and having a predetermined energy absorption characteristic; and,
   B. means for positioning said energy absorbing means between a scanning X-ray beam and a transmission intensity dectector of the apparatus.

2. The test body of claim 1 wherein said means for positioning said energy absorption means includes a housing supporting said layered arrays and means for supporting said housing in the apparatus at a location between the source of X-rays and the detector.

3. The test body of claim 2 wherein said housing comprises a shell having the general shape of a human body member for facilitating the positioning of said test body in a receptacle of the apparatus.

4. The test body of claim 3 wherein said shell has the shape of a human head.

5. The test body of claim 4 wherein said housing comprises a base plate, and said shell defines a plurality of cylindrically shaped recesses extending from said base plate, and a plurality of cross sectional arrays captivated by said recesses.

6. The test body of claim 5 wherein the tomographic scanning apparatus has an axis about which an X-ray source and detector are rotated, and said means for positioning said energy absorbing means positions said cylindrically shaped housing wall members concentrically with said axis.

7. The test body of claim 1 wherein each of said test elements is adapted for testing the capability of the apparatus to differentiate between objects at different contrast levels.

8. The test body of claim 7 wherein said test element comprises a ring shaped body.

9. The test body of claim 2 wherein said test element includes a test element body formed of an X-ray energy absorption material having a predetermined absorption characteristic and a plurality of bodies or voids positioned within said test element body having different absorption characteristics.

10. The test body of claim 9 wherein said test element is adapted for testing volume contrast sensitivity of said apparatus.

11. The test body of claim 10 wherein said test element body comprises a rectangular shaped bar and said plurality of internally located bodies or voids are spherically shaped, extend linearly within said bar, and are of different diameter.

12. The test body of claim 10 wherein said test element is adapted to detect the fidelity of the apparatus in reconstructing an image of the slice.

13. The test element of claim 12 wherein said test element comprises a rectangular shaped bar and said plurality of bodies are spherically shaped, are of substantially the same diameter, and extend linearly at an angle with respect to the direction of projection of an impinging X-ray beam.

14. The test body of claim 9 wherein said test element is adapted for testing the capability of the apparatus to distinguish between relatively small objects of differing sizes and contrasts.

15. The test body of claim 14 wherein the internally positioned bodies or voids are spherically shaped, have differing diameters, and have differing absorption characteristics.

16. The test body of claim 15 wherein said test element body is generally rectangular shaped and said internally located plurality of bodies or voids are arranged in a rectangular array within said test element body.

17. The test body of claim 1 wherein at least one of said test elements is adapted for testing the capability of the machine to distinguish between materials of different contrasts and wherein demarcation between the materials is not clearly defined.

18. The test body of claim 17 wherein said test element comprises first and second wedge segments of differing energy absorption characteristics.

19. The test body of claim 1 wherein at least one of said test elements is adapted to test the accuracy of the apparatus in distinguishing between objects of known absorption characteristics.

20. The test body of claim 19 wherein said test element comprises a bar of generally rectangular configuration and having a plurality of integral segments of differing absorption characteristics.

21. The test body of claim 1 wherein at least one of said test elements is adapted for testing the resolution of the apparatus.

22. The test body of claim 21 wherein said test element comprises a test element body having pairs of sheets of material, said pairs including first and second sheets of predetermined thicknesses, and said first and second sheets in a pair having different absorption characteristics.

23. The test body of claim 22 wherein the number of pairs per unit length varies in the direction of scoring.

24. The test body of claim 21 wherein said test element comprises a test element body of generally star shaped configuration having a hub and a plurality of segments extending radially from said hub.

25. The test body of claim 1 wherein at least one of said test elements is adapted for testing the modulation transfer function of the apparatus.

26. The test body of claim 25 wherein said test element comprises an elongated, cylindrically shaped wire.

27. The test body of claim 1 including means for providing a fluid bath and for receiving a sample specimen within said bath.

* * * * *